US007592596B2

(12) United States Patent
Klein et al.

(10) Patent No.: US 7,592,596 B2
(45) Date of Patent: Sep. 22, 2009

(54) METHODS AND SYSTEMS FOR MEDICAL IMAGING

(75) Inventors: Ytzhak Klein, Kiryat-Yam (IL); Yaron Hefetz, Herzeliya (IL); Alexander Gabriel Fishler, Haifa (IL); Michael Wilk, Haifa (IL)

(73) Assignee: GE Medical Systems Israel, Ltd, Tirat Hacarmel (IL)

( * ) Notice: Subject to any disclaimer, the term of this patent is extended or adjusted under 35 U.S.C. 154(b) by 594 days.

(21) Appl. No.: 11/144,120

(22) Filed: Jun. 3, 2005

(65) Prior Publication Data

US 2006/0276706 A1 Dec. 7, 2006

(51) Int. Cl.
*G01T 1/00* (2006.01)
*G01T 1/10* (2006.01)

(52) U.S. Cl. .............. 250/361 R; 250/362; 250/370.06; 250/370.09

(58) Field of Classification Search ............ 250/370.06, 250/370.09, 361 R, 362
See application file for complete search history.

(56) References Cited

U.S. PATENT DOCUMENTS

| 3,747,001 | A |   | 7/1973  | Fasching et al. |
| 4,246,652 | A | * | 1/1981  | Khan et al. ................... 367/42 |
| 4,491,733 | A |   | 1/1985  | Wasserman |
| 4,767,929 | A |   | 8/1988  | Valentine |
| 4,779,077 | A | * | 10/1988 | Lichtblau ................. 340/572.4 |
| 5,270,547 | A | * | 12/1993 | Stark et al. ................... 250/369 |
| 5,393,982 | A | * | 2/1995  | Mott et al. ............. 250/370.06 |
| 5,583,635 | A | * | 12/1996 | Miura et al. ................. 356/338 |
| 5,866,907 | A | * | 2/1999  | Drukier et al. .............. 250/366 |
| 5,952,662 | A |   | 9/1999  | McDaniel |
| 6,252,232 | B1 |  | 6/2001  | McDaniel et al. |
| 6,310,349 | B1 |  | 10/2001 | Wong et al. |
| 6,525,322 | B2 |  | 2/2003  | Wong et al. |
| 6,590,957 | B1 |  | 7/2003  | Warburton et al. |

FOREIGN PATENT DOCUMENTS

GB 2135451 A 8/1984
WO WO 90/13829 11/1990

OTHER PUBLICATIONS

Benulis, C.A. and McFarlane, W.K.; "*A Subnanosecond Time Discrimator System*"; Nuclear Instruments and Methods in Physics Research A240 (1985) pp. 130-134.
International Search Report; PCT/IB2006/003969; p. 3.

* cited by examiner

*Primary Examiner*—David P Porta
*Assistant Examiner*—Casey Bryant
(74) *Attorney, Agent, or Firm*—Dean D. Small; The Small Patent Law Group

(57) ABSTRACT

Methods and systems for a medical imaging system are provided. The medical imaging system includes an input circuit configured to receive a voltage level signal indicative of a stream of pulses, a voltage level signal shape analyzer configured to determine shape characteristics of the received voltage level signal and an amount of time that the received voltage level signal matches a predetermined shape, and a counting circuit configured to determine a true number of pulses from the shape characteristics and the amount of time.

24 Claims, 6 Drawing Sheets

METHODS AND SYSTEMS FOR MEDICAL IMAGING

BACKGROUND OF THE INVENTION

This invention relates generally to imaging and, more particularly, to emissions tomography imaging.

At least some known x-ray or nuclear "photon counting" tomography systems have limited count capabilities due to a width of an analog detection signal (about 150-200 nanoseconds or more). The width of the analog signal generally depends on the detector used. An x-ray detector may have a signal width of approximately 150-200 nanoseconds, but a Sodium Iodide (NaI) scintillation crystal, used in gamma cameras, may produce temporally longer pulses than a Bismuth Germanate (BGO) scintillation crystal commonly used in positron emission tomography (PET). In relatively high-count rates, individual pulses representing individual detection events may "pile-up" or arrive at detection circuitry at a rate that exceeds the counting capability of the detection circuitry, for example, a comparator may not have time to return to a low or zero level before a next pulse arrives. Accordingly, a plurality of pulses may be counted as a single event.

At least some known imaging systems use count rate correction methods to attempt to accurately determine pulses due to each individual detection. A function of a "true count rate" vs. a "measured count rate" may be found experimentally, for example, using a strong radioactive source with a known decay time and measuring the count rate over a long duration, or may be calculated from a theoretical model of the detector, trigger, and counter system. However, such methods only statistically correct the count rate and consequently add noise to the signal. Such methods do not recover the lost count.

For example, for a random distribution of pulses, if the statistical noise associated with N counted pulses is $N^{1/2}$, the Signal to Noise Ratio (SNR) may be shown to be $1/N^{1/2}$. Assuming a non-buffered triggering system, at true rate, T, pulses per second, the measured rate will be $T*e^{-2*T/R}$, where R is the characteristic rate of the system. When the true rate, T is relatively low, T<<R, then the measured rate (M) is given by $M=T*e^{-2*T/R} \sim T$ For relatively higher count rates, the equation has to be solved to yield T from knowing M, from, for example, a lookup table. However, the SNR associated with the calculated T is at least as large as $1/M^{1/2}$, which is worse than $1/T^{1/2}$.

BRIEF DESCRIPTION OF THE INVENTION

In one aspect, a medical imaging system is provided. The medical imaging system includes an input circuit configured to receive a voltage level signal indicative of a stream of pulses, a voltage level signal shape analyzer configured to determine shape characteristics of the received voltage level signal and an amount of time that the received voltage level signal matches a predetermined shape, and a counting circuit configured to determine a true number of pulses from the shape characteristics and the amount of time.

In another aspect, a count rate correction circuit for a medical imaging system is provided. The circuit includes an input circuit configured to receive a voltage level signal comprising a plurality of temporally-spaced peaks, each peak associated with a pulse from an x-ray detector, a voltage level signal shape analyzer configured to determine shape characteristics of the received voltage level signal and an amount of time that the received voltage level signal matches a predetermined shape, and a counting circuit configured to determine a true number of pulses from the shape characteristics and the amount of time.

In yet another aspect, a method of correcting a count rate of randomly occurring pulses is provided. The method including receiving a plurality of pulses, converting the plurality of pulses to a voltage level signal, determining a shape characteristic of a portion of the voltage level signal that corresponds to at least one pulse, and determining a true pulse count rate of the received plurality of pulses using the determined shape characteristic and a predetermined factor.

DETAILED DESCRIPTION OF THE INVENTION

Figure 1:
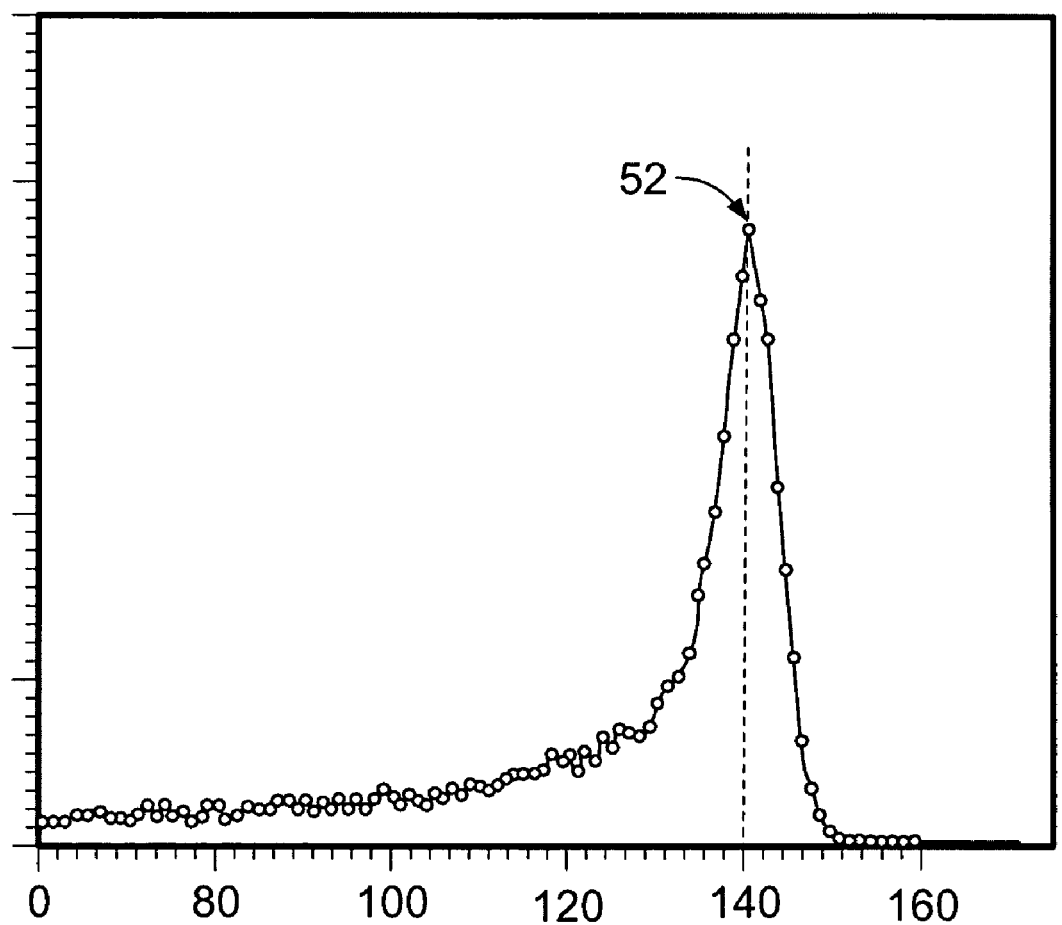
FIG. 1 is a graph that illustrates an exemplary energy spectrum of a single pixel of a pixilated CZT detector.

FIG. 1 is a graph 50 that illustrates an exemplary energy spectrum of a single pixel of a pixilated CZT detector exposed to substantially unscattered 140 keV gamma rays. Graph 50 includes an x-axis graduated in units of keV and a y-axis representative of an amount of total counts or count rate observed at each keV level. An energy spectrum peak 52 centered about 140 keV represents the gamma rays that have been absorbed substantially within a central region portion of the single pixel. The distribution of signal amplitudes of these events is approximately Gaussian. However, a significant number of gamma rays are also detected in the portion of the energy response spectrum that tails toward the lower energies. This tail effect is caused, in part, by Compton scattering, by gamma ray absorption events that do not confine all charge creation to within a single pixel and by non-ideal charge collection. Because the illustrated response function represents the distribution of measured signals from only a single pixel, charge that is lost from the pixel and shared with adjacent pixels is not included in the response function. As a result, gamma ray absorption events in which the charge collection is incomplete due to charge sharing with other pixels are lost from the peak region and contribute to the low energy tailing. When an X-Ray tube is used as a source of radiation, such as in X-Ray imaging or Computed Tomography (CT), the radiation source has a broad energy spectra which is convolved with the detector spectral response.

Figure 2:
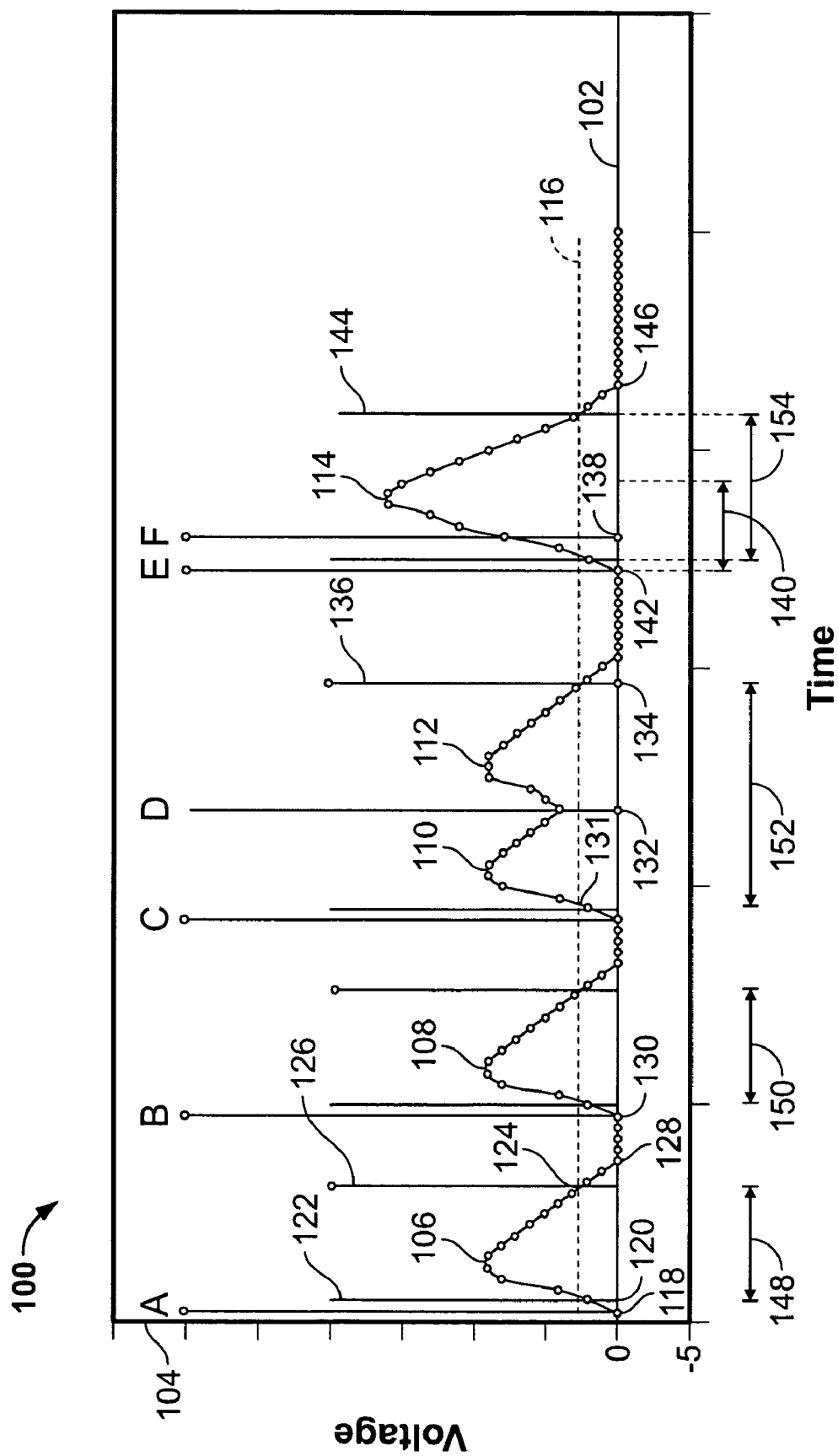
FIG. 2 is a graph of an exemplary stream of random pulses and an associated electrical circuit response.

FIG. 2 is a graph 100 of an exemplary stream of random pulses and an associated electrical circuit response. Graph 100 includes an x-axis 102 graduated in units of time, for example nanoseconds or microseconds, and a y-axis 104 graduated in units of signal strength or magnitude, for example, voltage. A plurality of incoming pulses A, B, C, D, E, and F represent substantially randomly timed events, such as a detection of an incident photon upon a scintillator crystal, which converts an interaction of the photon with the molecules of the crystal into a burst of light that may be proportional to an energy of the photon, a location of the interaction within the crystal and photo characteristics of the crystal material. The burst of light may be detector by a detector, for example, but not limited to, a photomultiplier tube (PMT). The PMT detects the burst of light and generates an output signal that is proportional to the amount of light received. In an alternative embodiment, the photon may interact with a detector that includes a solid-state crystal, for example, but not limited to Cadmium Zinc Telluride (CZT), that converts the photon interaction to an output signal directly. In the exemplary embodiment, a plurality of voltage peaks 106, 108, 110, 112, and 114 are associated with pulses A, B, C, D, and the combination of pulses E, and F, respectively. A threshold 116 may be set such that a voltage level of the voltage peaks associated with each pulse may be required to exceed the threshold level to be counted and the voltage level associated with the voltage peaks may be required to return to a value less than the threshold level before the counter is reset so as to be ready to count the next incoming pulse.

In the exemplary embodiment, the voltage output associated with pulse A begins to increase at point 118. At point 120 the voltage output associated with pulse A exceeds threshold 116 and an upward threshold crossing trigger response 122 may be generated. The upward threshold crossing trigger response 122 may be used to increment a pulse counter that tabulates the total number of proper level pulses received. The voltage continues to increase according to characteristics of the scintillation crystal and PMT, or the solid-state crystal to a peak at point 106. The voltage output then tails off at a characteristic rate through threshold 116 at a point 124 where a downward threshold crossing trigger response 126 may be generated. The voltage output may tail off, as is characteristic of detectors comprising CZT. The downward threshold crossing trigger response 126 may be used to reset the pulse counter to allow subsequent incoming pulses to be counted. The voltage output continues to decrease back to an approximately zero voltage level at point 128. At point 130, a next pulse may begin the sequence again to count pulse B. Using threshold 116 ensures only pulses of sufficient predetermined magnitude are counted. A pulse that does not represent a photon/crystal interaction, such as circuit noise may not generate sufficient voltage to reach threshold 116 and thus, will not be counted.

It may happen, by chance, that two pulses will arrive at the detector nearly at the same time, such as the illustrated pulses C and D. In this case, the signal of the second pulse is "piled up" on top of the first signal. This pile-up may happen even at low rate, but the chance of pile-up increases when the rate increases. When pulses arrive at a rate that exceeds the ability of the voltage output to decay back below threshold 116 between pulses, two incoming pulses may only be counted as one pulse. Such is the case of pulses C and D. After pulse C arrives and the output voltage associated with pulse C increases to threshold 116 and generates an upward threshold crossing trigger response at a point 131, the output voltage continues to increase to peak 110. The output voltage then decays until a point 132 when pulse D arrives and generates a voltage output before the voltage level can decay back below threshold 116. The voltage level increases to peak 112 before finally decaying to below threshold 116 at a point 134, where a downward threshold crossing trigger response 136 may be generated.

In another example, pulses may arrive at such a rate that a next incoming pulse, such as pulse F at a point 138, may arrive during a period 140 when the voltage output is increasing due to the arrival of the previous pulse E at a point 142. In such a case, the associated peak 114 may be uncharacteristically high relative to the voltage output associated with pulses A, B, C, and D. A downward threshold crossing trigger response 144 may be generated after the voltage output decays from peak 114 and crosses threshold 116 in a decreasing direction toward an approximately zero voltage output level at point 146.

A period 148 of an output voltage level peak may be considered a time period between, for example, upward threshold crossing point 120 and downward threshold crossing point 124. A period 150 associated with peak 108 will be approximately equal to period 148 because each output voltage was permitted to decay to approximately zero before a next pulse arrived. A period 152 results when two pulses C and D overlap with second pulse D arriving after first pulse C has reached peak 110. In the exemplary case of pulses C and D, period 152 is longer than periods 148 and 150, and the amplitude of peaks 110 and 112 are approximately equal in amplitude to peaks 106 and 108. A period 154 results when two pulses E and F overlap with second pulse F arriving before first pulse E has reached a peak. In the exemplary case of pulses E and F, period 152 may be approximately equal to periods 148 and 150 or may be longer than periods 148 and 150, and the amplitude of peak 114 is greater than the amplitude of peaks 106 and 108.

A medical imaging system using a simple threshold detection scheme may correctly account for pulses A and B but counts the pile-up of pulses C and D as well as of pulses E and F as one pulse each to a total of 4 counts versus 6 pulses that were actually received. When pulses are of uneven strength and mixed with detector noise, the range of triggering threshold may be limited due to false counts or missing counts that may occur if threshold 116 is set too low or too high, respectively.

In an alternative embodiment, the voltage output is analyzed by a pulse shape analyzer, which estimates the true number of pulses that causes the measured voltage output. For example, the pulse analyzer may have a single threshold trigger and a pulse duration measuring unit. The time measurement may be based on, for example, a Time to Amplitude (TAC) unit that converts the time between up-going threshold crossing and down-going threshold crossing to voltage. In an alternative embodiment, the time measuring unit may be based on counting oscillator pulses as described herein. If the period of the voltage output peak signal is longer than a predetermined value, for example, period 152, associated with overlapped pulses C and D, the signal is estimated to include two pulses, and if the period of the voltage output peak signal is longer than twice duration of period 152 then the signal may be estimated to include three pulses, and so on.

In another alternative embodiment, the pulse analyzer may have a signal level-measuring unit, for example a peak-and-hold unit. If the signal level is above a predetermined value, such as peak 114 associated with pulses E and F, the signal is estimated to include two pulses. The signal level-measuring unit may include a plurality of different threshold levels, such that a pile-up of greater than two pulses may be detected and corrected. A combination of peak duration time measurement and peak amplitude measurement may be used to estimate a plurality of incoming pulses for each measured pulse. The signal level may be compared to the thresholds only if the pulse duration exceeds a predetermined level. Additionally, the peak duration time may be examined only if a second or greater signal level threshold was triggered. Further, the number of pulses estimated may depend upon the duration of the time period of the measured pulses and/or the height of the amplitude of the measured pulses. To generate a statistical best estimate of the number of pulses from the number of measured pulses and the voltage output peak characteristics a fractional number of pulses may be estimated. For example, 1.7 pulses may be designated as the best estimation to the number of pulses that are associated with a signal shape. The pulse count rate may be corrected during the counting process or may be corrected afterward during a correction process using a determined correction factor wherein the correction factor is based on the above described methods.

Figure 3:
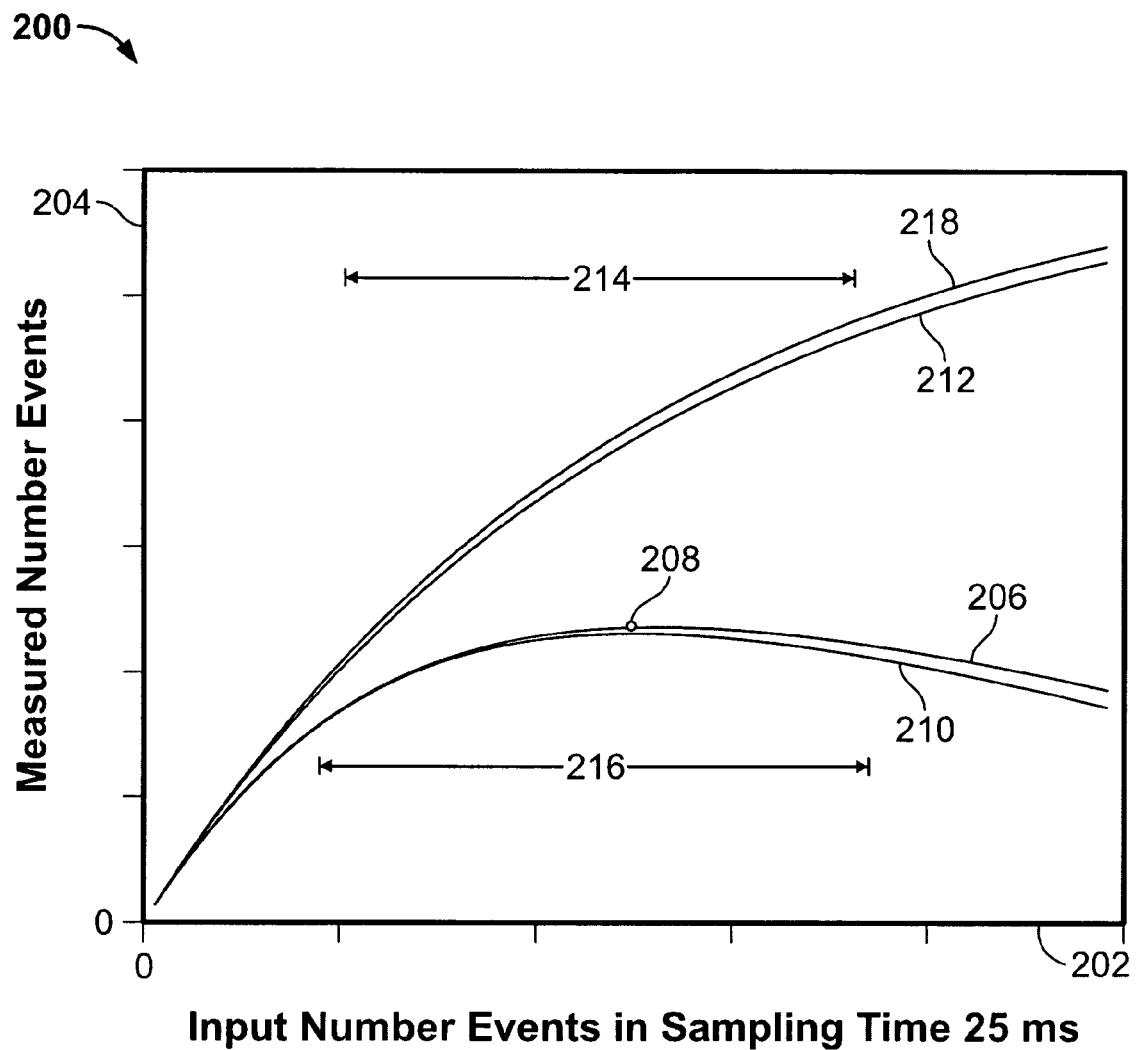
FIG. 3 is a graph of an exemplary comparison between a number of true pulses and a number of measured pulses for an exemplary medical imaging system.

FIG. 3 is a graph 200 of an exemplary comparison between a number of true pulses and a number of pulses that are measured for a medical imaging system. Graph 200 includes an x-axis 202 graduated in units a number of events in a selectable sampling time and a y-axis 204 graduated in units of a measured number of counts in the twenty-five millisecond time interval. A trace 206 represents an output of a mean paralyzed result of a simulation of an exemplary known method. Trace 206 represents an output of the average number of measured photons in the 25 milli-second time interval. As the input rate increases, the output increases, until a point 208 is reached wherein for a further increase in the input rate, the output decreases indicating a paralyzation of the counting circuitry. A trace 210 represents an output representative of a theoretical paralyzed result as given by:

$$N_p = N_i * e^{-\lambda\tau}, \text{ where} \quad (1)$$

$N_p$ is a mean measured paralyzed result,
$N_i$ is an input number of photons,
$\lambda$ is an input rate, and
$\tau$ is an average pulse length.

The simulation using equation (1) showed good correlation with the theoretical output rate for trace 206.

A trace 212 represents an output of a mean non-paralyzed result using an embodiment of the present invention. Trace 212 represents an average number of output events in the 25 millisecond time interval. Trace 212 includes a substantially linear portion 214 that is significantly more linear than a corresponding portion 216 for traces 206 and 210. A trace 218 represents an output representative of a theoretical non-paralyzed result as given by an output of a theoretical non-paralyzed result using:

$$N_n = \frac{T}{\tau}(1 - e^{-\lambda\tau}), \text{ where} \quad (2)$$

$N_n$ is a mean measured non-paralyzed result,
T is a sampling time,
$\lambda$ is an input rate, and
$\tau$ is an average pulse length.

As illustrated in graph 200, trace 218 substantially correlates with the simulation results illustrated by trace 212.

$\tau$ is an average pulse length that represents the average duration that a comparator is in an 'on' state in response to a single photon. The distribution of durations may be due to input photons energy variations and may be determined experimentally. Accordingly, an estimate an actual rate of arriving photons may be determined using:

$$\lambda = \text{Ln}\left(1 - \frac{\tau}{T}\right), \text{ where} \quad (3)$$

T is a sampling time,
$\lambda$ is an input rate, and
$\tau$ is an average pulse length.

Figure 4:
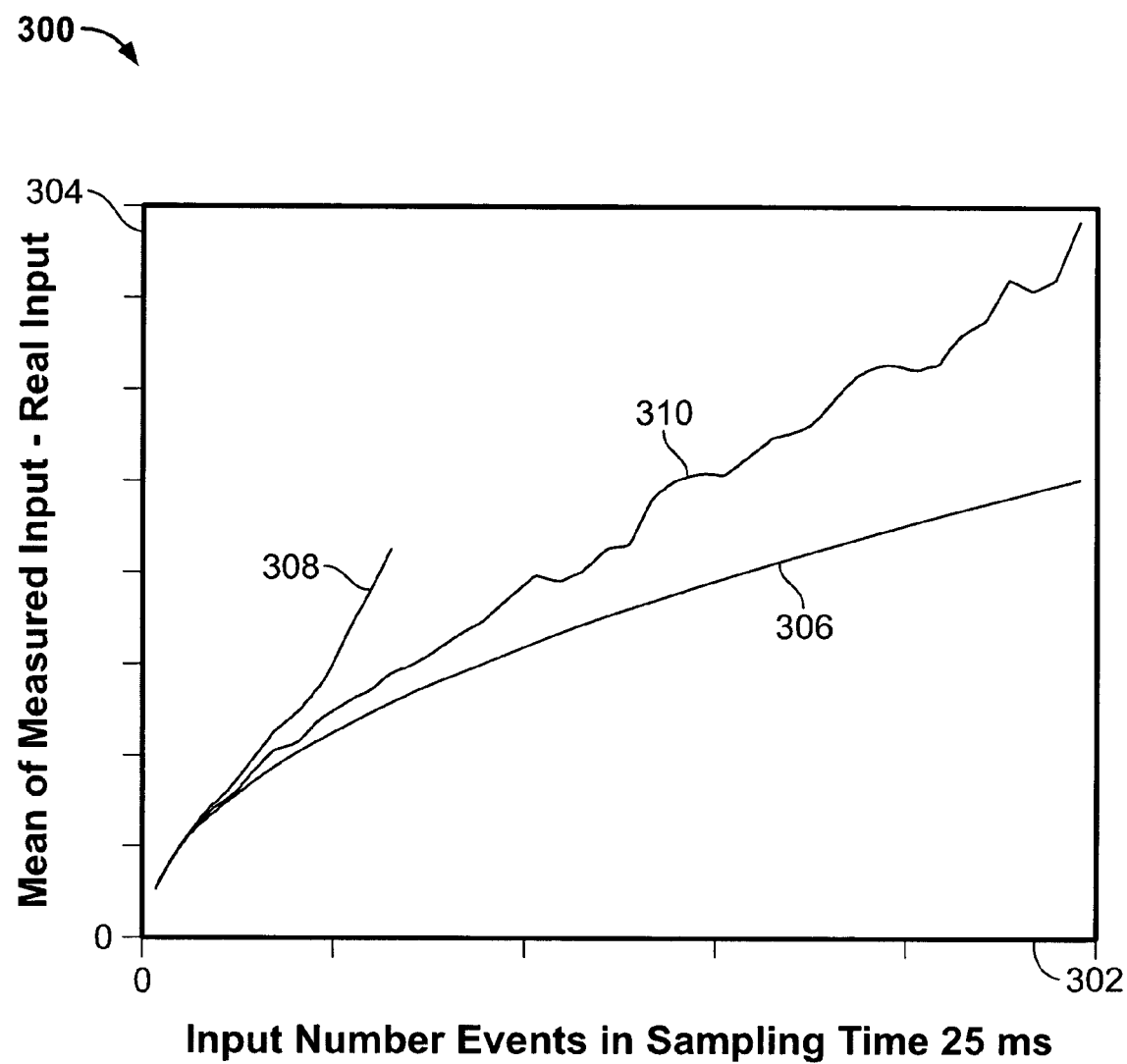
FIG. 4 is a graph of a comparison of an estimated number of input photons for an exemplary known detection system, an estimated number of input photons using a detection system in accordance with an exemplary embodiment of the present invention, and a square root of the input rate.

FIG. 4 is a graph 300 of a comparison of an estimated number of input photons for an exemplary known detection system, an estimated number of input photons using a detection system in accordance with an exemplary embodiment of the present invention, and a square root of the input rate. Graph 300 includes an x-axis 302 graduated in units a number of events in a selectable sampling time and a y-axis 304 graduated in units of a measured number of counts in the twenty-five millisecond time interval. A trace 306 represents an inaccuracy due to the input Poisson statistics. This is unavoidable error that serves as a lower limit to any measurement method. A trace 308 represents an inaccuracy using the exemplary known method. A trace 310 represents an inaccuracy using a method in accordance with an exemplary embodiment of the present invention. It should be appreciated that in low rates all errors are small and similar, at high rate, the method in accordance with an exemplary embodiment of the present invention is superior to the known method.

Figure 5:
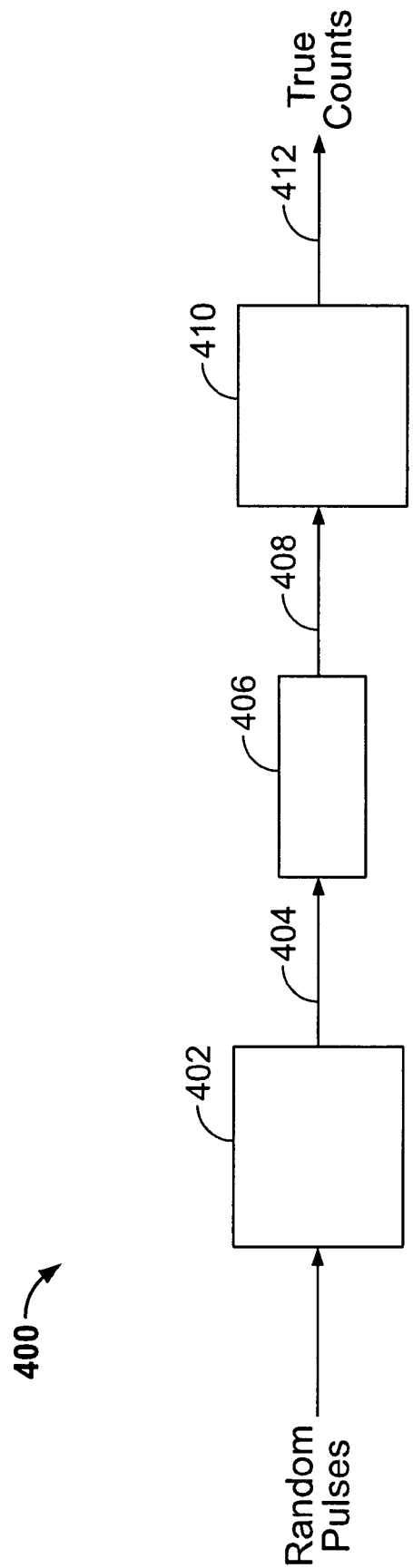
FIG. 5 is a block diagram of an exemplary embodiment of a pulse rate correction circuit of a medical imaging system.

FIG. 5 is a block diagram of an exemplary embodiment of a circuit 400 of a medical imaging system that may used to implement the random pulse counting methods described herein. In the exemplary embodiment, circuit 400 includes a pulse shape analyzer 402 that receives an input signal, such as a stream of random pulses from, for example, one or more x-ray and/or gamma detectors (not shown). Pulse shape analyzer 402 generates an output 404 that is a function of the counts arriving from the detectors. A counter 406 receives output 404 and generates an output 408 indicative of the number of counts received from output 404. A rate correction circuit 410 may be used to apply an estimate of the number incoming pulses for each measured pulse using a combination of peak duration time measurement and amplitude measurement. Accordingly, the number of pulses estimated may depend upon the duration of the time period of the measured pulses and/or the height of the amplitude of the measured pulses. To generate a correction for the number of pulses from the number of measured pulses and the voltage output peak characteristics a fractional number of pulses may be estimated. Rate correction circuit 410 outputs a true count output signal 412 that may be used by the medical imaging system.

Figure 6:
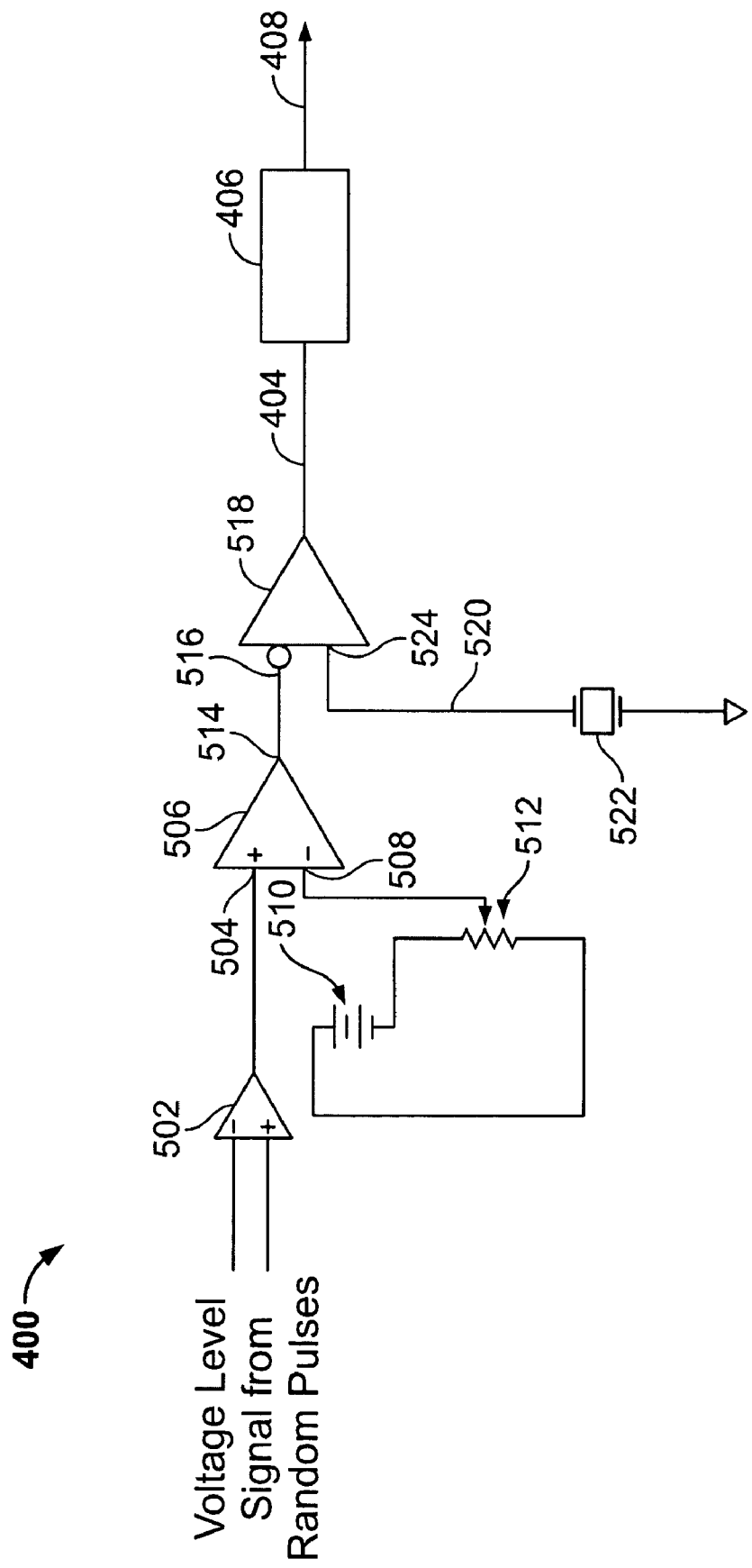
FIG. 6 is a schematic diagram of an exemplary embodiment of the pulse rate correction circuit shown in FIG. 5.

FIG. 6 is a schematic diagram of an exemplary embodiment of circuit 400 (shown in FIG. 5). In the exemplary embodiment, a high input impedance circuit 502, such as a operational amplifier receives an input signal, such as a stream of random pulses from, for example, one or more x-ray and/or gamma detectors. The conditioned signal is transmitted to a first input 504 of a comparator circuit 506. A threshold value may be transmitted to a second input 508 of comparator circuit 506. In the exemplary embodiment, the threshold value is selectable based on the voltage of a voltage source 510, such as a battery, and the resistance settings of a voltage divider 512, such as a potentiometer. An output 514 of comparator 506 is coupled to an inverted enable input 516 of a gate with enable circuit 518. An output 520 of an oscillator 522 is coupled to an input 524 of gate with enable circuit 518. Output 404 from gate with enable circuit 518 is coupled to counter 406.

In operation, incoming random pulses are compared to a selectable threshold such that a gate signal is enabled and disabled when the magnitude of each incoming pulse signal is below or above the selected threshold value. During the time gate with enable circuit 518 is enabled, output 404 is counted by counter 406 to determine an amount of time that the current pulse has exceeded the threshold. The time value may be used to estimate a number of true pulses that were received during the current pulse duration. The setting of the threshold may be used in combination with the duration count to farther estimate a number of true pulses that were received during the current pulse duration.

The above-described methods and systems for medical imaging using a multi-modality medical imaging system including an integrated gantry having a plurality of imaging detector rotors coupled to a single stator is cost-effective and highly reliable for imaging a patient. More specifically, the methods and systems described herein facilitate the benefits of multi-modality imaging in a system having a relatively small footprint. As a result, the methods and systems described herein facilitate imaging a patient in a cost-effective and reliable manner.

Exemplary embodiments of medical imaging systems and methods are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A medical imaging system comprising: an input circuit configured to receive a voltage level signal indicative of a stream of pulses;
    a voltage level signal shape analyzer configured to determine, directly from the received voltage level signal, shape characteristics of the received voltage level signal and an amount of time that the received voltage level signal matches a predetermined shape; and
    a counting circuit configured to estimate a true number of pulses from the shape characteristics and the amount of time.

2. A medical imaging system in accordance with claim 1 further comprising a gating circuit configured to determine the amount of time that the received voltage level signal matches the predetermined shape.

3. A medical imaging system in accordance with claim 1 further comprising a comparator circuit configured to determine a magnitude of the voltage level signal relative to a predetermined threshold.

4. A medical imaging system in accordance with claim 1 wherein said input circuit further comprises a converter configured to convert the stream of pulses to the voltage level signal.

5. A medical imaging system in accordance with claim 4 wherein said converter is configured to convert a stream of light pulses to a voltage level signal.

6. A medical imaging system in accordance with claim 4, wherein the medical imaging system further comprises an x-ray detector configured to convert a stream of light pulses to the voltage level signal, said converter is configured to receive the voltage level signal.

7. A medical imaging system in accordance with claim 1 wherein said voltage level signal shape analyzer is configured to count time when a magnitude of the voltage level signal exceeds a predetermined threshold.

8. A medical imaging system in accordance with claim 1 wherein said voltage level signal shape analyzer is configured to measure a magnitude of the voltage level signal.

9. A medical imaging system in accordance with claim 1 wherein said voltage level signal shape analyzer is configured to measure a time duration for the magnitude of the voltage level signal to change between a first magnitude and a second magnitude.

10. A medical imaging system in accordance with Claim 1 wherein said voltage level signal shape analyzer is configured to count pulses in an oscillator output.

11. A medical imaging system in accordance with claim 1 wherein said voltage level signal shape analyzer is configured to count time between the voltage level signal crossing the threshold in a first direction and the voltage level signal crossing the threshold in a second direction wherein the second direction is different than the first direction.

12. A medical imaging system in accordance with claim 1 wherein said a counting circuit is further configured to estimate an actual rate of arriving photons using:

$$\lambda = -\frac{\operatorname{Ln}\left(1 - \frac{N_n * \tau}{T}\right)}{\tau}, \text{ where}$$

$N_n$ is a mean measured non-paralyzed result,
T is a sampling time,
$\lambda$ is an input rate, and
$\tau$ is an average pulse length.

13. A count rate correction circuit for a medical imaging system, said circuit comprising:
    an input circuit configured to receive a voltage level signal comprising a plurality of temporally-spaced peaks, each peak associated with a pulse from an x-ray detector;
    a voltage level signal shape analyzer configured to determine, directly from the received voltage level signal, shape characteristics of the received voltage level signal and an amount of time that the received voltage level signal matches a predetermined shape; and
    a counting circuit configured to determine a true number of pulses from the shape characteristics and the amount of time.

14. A count rate correction circuit in accordance with claim 13 wherein said a counting circuit is further configured to estimate an actual rate of arrival of the plurality of temporally-spaced peaks using:

$$\lambda = -\frac{\operatorname{Ln}\left(1 - \frac{N_n * \tau}{T}\right)}{\tau}, \text{ where}$$

$N_n$ is a mean measured non-paralyzed result,
T is a sampling time,
$\lambda$ is an input rate, and
$\pi$ is an average pulse length.

15. A method of correcting a count rate of randomly occurring pulses, said method comprising:
    receiving a plurality of pulses;
    converting the plurality of pulses to a voltage level signal;
    determining, directly from the voltage level signal, a shape characteristic of a portion of the voltage level signal that corresponds to at least one pulse; and
    determining a true pulse count rate of the received plurality of pulses using the determined shape characteristic and a predetermined factor.

16. A method in accordance with claim 15 wherein determining a shape characteristic of the voltage level signal comprises counting time when a magnitude of the voltage level signal exceeds a predetermined threshold.

17. A method in accordance with claim 16 wherein counting time when a magnitude of the voltage level signal exceeds a predetermined threshold comprises counting pulses in an oscillator output.

18. A method in accordance with claim 16 wherein counting time when a magnitude of the voltage level signal exceeds a predetermined threshold comprises counting time between the voltage level signal crossing the threshold in a first direction and the voltage level signal crossing the threshold in a second direction wherein the second direction is different than the first direction.

19. A method in accordance with claim 18 further comprising:
comparing the counted time to a predetermined threshold time; and
incrementing the pulse count by a multiple amount using the comparison.

20. A method in accordance with claim 18 wherein counting time when a magnitude of the voltage level signal exceeds a predetermined threshold further comprising converting the counted time to a voltage level representative of the counted time.

21. A method in accordance with claim 20 further comprising:
comparing the voltage level to a predetermined threshold voltage level; and
incrementing the pulse count by a multiple amount using the comparison.

22. A method in accordance with claim 15 wherein determining a shape characteristic of the voltage level signal comprises measuring a magnitude of the voltage level signal.

23. A method in accordance with claim 15 wherein determining a shape characteristic of the voltage level signal comprises measuring a time duration for the magnitude of the voltage level signal to change between a first magnitude and a second magnitude.

24. A method in accordance with claim 15 further comprising estimating an actual rate of the plurality of arriving pulses using:

$$\lambda = -\frac{\operatorname{Ln}\left(1 - \frac{N_n * \tau}{T}\right)}{\tau}, \text{ where}$$

$N_n$ is a mean measured non-paralyzed result,
T is a sampling time,
$\lambda$ is an input rate, and
$\pi$ is an average pulse length.

* * * * *

UNITED STATES PATENT AND TRADEMARK OFFICE
CERTIFICATE OF CORRECTION

PATENT NO. : 7,592,596 B2  Page 1 of 1
APPLICATION NO. : 11/144120
DATED : September 22, 2009
INVENTOR(S) : Klein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 945 days.

Signed and Sealed this

Twenty-first Day of September, 2010

David J. Kappos
*Director of the United States Patent and Trademark Office*